US00PP20662P2

(12) United States Plant Patent
van der Knaap

(10) Patent No.: US PP20,662 P2
(45) Date of Patent: Jan. 19, 2010

(54) *KALANCHOE* PLANT NAMED 'DON DARCIO'

(50) Latin Name: *Kalanchoe blossfeldiana*
Varietal Denomination: Don Darcio

(75) Inventor: Leonardus Johannus Maria van der Knaap, Naaldwijk (NL)

(73) Assignee: Knaap Licenties B.V., Naaldwijk (NL)

( * ) Notice: Subject to any disclaimer, the term of this patent is extended or adjusted under 35 U.S.C. 154(b) by 0 days.

(21) Appl. No.: 12/283,262

(22) Filed: Sep. 8, 2008

(51) Int. Cl.
*A01H 5/00* (2006.01)

(52) U.S. Cl. ..... Plt./339

(58) Field of Classification Search ..... Plt./339
See application file for complete search history.

(56) References Cited

U.S. PATENT DOCUMENTS

PP6,296 P * 9/1988 Van der Knaap ..... Plt./339
PP12,593 P2 * 4/2002 Drewlow ..... Plt./339
PP17,949 P2 * 8/2007 van der Knaap ..... Plt./338

OTHER PUBLICATIONS

Plant varieties Journal #69, Oct. 2008. Available at: http://www.cfia-acia.agr.ca/english/plaveg/pbrpov/journal/appsaccept69e.shtml.*
UPOV ROM GTITM Computer Database, GTI Jouve Retrieval Software 2008/06 Citations for 'Don Darcio'.*
Shaw, JMH. "An investigation of the cultivated *Kalanchoe daigremontiana* group, with a checklist of *Kalanchoe* cultivars." Haniburyana 3: pp. 17-79 (2008) (Royal Horticultural Society).*

* cited by examiner

*Primary Examiner*—Wendy C. Haas
(74) *Attorney, Agent, or Firm*—C. A. Whealy

(57) ABSTRACT

A new and distinct cultivar of *Kalanchoe* plant named 'Don Darcio', characterized by its upright, uniform and vigorous growth habit; freely branching habit; dark green-colored leaves; uniform and freely flowering habit; double pink-colored flowers; and excellent postproduction longevity.

2 Drawing Sheets

Botanical designation: *Kalanchoe blossfeldiana.*
Cultivar denomination: 'Don Darcio'.

BACKGROUND OF THE INVENTION

The present invention relates to a new and distinct cultivar of *Kalanchoe*, botanically known as *Kalanchoe blossfeldiana*, and hereinafter referred to by the name 'Don Darcio'.

The new *Kalanchoe* plant is a product of a planned breeding program conducted by the Inventor in Naaldwijk, The Netherlands. The objective of the breeding program is to create new double-flowered *Kalanchoe* cultivars with attractive foliage and flower coloration.

The new *Kalanchoe* plant originated from a cross-pollination made by the Inventor in Naaldwijk, The Netherlands in December, 2002, of a proprietary selection of *Kalanchoe blossfeldiana* identified as code No. 2000033, not patented, as the female, or seed parent with a proprietary selection of *Kalanchoe blossfeldiana* identified as code No. 20000153-2, not patented, as the male, or pollen, parent. The cultivar Don Darcio was discovered and selected by the Inventor as a flowering plant from within the progeny of the stated cross-pollination in a controlled greenhouse environment in Naaldwijk, The Netherlands in October, 2006.

Asexual reproduction of the new *Kalanchoe* by vegetative terminal cuttings in a controlled greenhouse environment in Naaldwijk, The Netherlands since January, 2007 has shown that the unique features of this new *Kalanchoe* plant are stable and reproduced true to type in successive generations.

SUMMARY OF THE INVENTION

Plants of the new *Kalanchoe* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Don Darcio'. These characteristics in combination distinguish 'Don Darcio' as a new and distinct cultivar of *Kalanchoe:*

1. Upright, uniform and vigorous growth habit.
2. Freely branching habit.
3. Dark green-colored leaves.
4. Uniform and freely flowering habit.
5. Double pink-colored flowers.
6. Excellent postproduction longevity.

Plants of the new *Kalanchoe* can be compared to plants of the female parent selection. Plants of the new *Kalanchoe* differ primarily from plants of the female parent selection in flower color as plants of the female parent selection have purple-colored flowers.

Plants of the new *Kalanchoe* can also be compared to plants of the male parent selection. Plants of the new *Kalanchoe* differ from plants of the male parent selection in the following characteristics:

1. Plants of the new *Kalanchoe* have double flowers whereas plants of the male parent selection have single flowers.
2. Plants of the new *Kalanchoe* and the male parent selection differ in flower color as plants of the male parent selection have yellow-colored flowers.

Plants of the new *Kalanchoe* can be compared to plants of the *Kalanchoe blossfeldiana* 'Don Frederico', disclosed in U.S. Plant Pat. No. 17,949. In side-by-side comparisons conducted in Naaldwijk, The Netherlands, plants of the new *Kalanchoe* differed from plants of 'Don Frederico' in the following characteristics:

1. Leaves of plants of the new *Kalanchoe* had more rounded apices and bases than leaves of plants of 'Don Frederico'.
2. Flowers of plants of the new *Kalanchoe* were pink in color whereas flowers of plants of 'Don Frederico' were yellow in color.

BRIEF DESCRIPTION OF THE PHOTOGRAPHS

The accompanying colored photographs illustrate the overall appearance of the new *Kalanchoe*, showing the colors as true as it is reasonably possible to obtain in colored reproductions of this type. Colors in the photographs may differ slightly from the color values cited in the detailed botanical description which accurately describe the colors of the new *Kalanchoe*.

The photograph on the first sheet comprises a side perspective view of a typical flowering plant of 'Don Darcio' grown in a container.

The photograph on the second sheet comprises close-up views of typical flower (top), a typical inflorescence (center) and the upper and lower surfaces of typical leaves (bottom).

DETAILED BOTANICAL DESCRIPTION

The aforementioned photographs and following observations, measurements and values describe plants grown in Naaldwijk, The Netherlands in a glass-covered greenhouse during the summer and under conditions which closely approximate commercial production. During the production of the plants, day temperatures ranged from 20° C. to 30° C., night temperatures ranged from 18° C. to 25° C. and light levels ranged from 5 kilolux to 60 kilolux. Plants grown in 12-cm containers received long day/short night conditions (more than 14 hours of light) for about three weeks; plants then received photoinductive short day/long night conditions (minimum 14 hours darkness) until flowering. Plants had been growing for 14 weeks when the photographs and the description were taken. In the detailed description, color references are made to The Royal Horticultural Society Colour Chart, 2001 Edition, except where general terms of ordinary dictionary significance are used.

Botanical classification: *Kalanchoe blossfeldiana* 'Don Darcio'.

Parentage:

*Female, or seed, parent.*—Proprietary selection of *Kalanchoe blossfeldiana* identified as code number 2000033, not patented.

*Male or pollen parent.*—Proprietary selection of *Kalanchoe blossfeldiana* identified as code number 20000153-2, not patented.

Propagation:

*Type.*—By vegetative terminal cuttings.

*Time to initiate roots, summer.*—About ten days at temperatures of 21° C.

*Time to initiate roots, winter.*—About two weeks at temperatures of 21° C.

*Time to produce a rooted young plant, summer.*—About three weeks at temperatures of 21° C.

*Time to produce a rooted young plant, winter.*—About four weeks at temperatures of 21° C.

*Root description.*—Fine, fibrous; white in color.

*Rooting habit.*—Freely branching; dense.

Plant description:

*Plant habit.*—Upright, uniform and vigorous growth habit. Very freely flowering with numerous compound cymes. Inverted triangle with rounded crown. Appropriate for 10-cm to 13-cm containers.

*Plant height at flowering.*—About 20 cm to 22 cm.

*Plant diameter at flowering.*—About 22 cm to 25 cm.

Lateral branch description:

*Branching habit.*—Freely branching habit; usually about twelve lateral branches develop per plant.

*Length.*—About 12 cm to 14 cm.

*Diameter.*—About 1 cm.

*Internode length.*—About 1 cm.

*Aspect.*—Erect.

*Strength.*—Strong.

*Texture.*—Smooth, glabrous.

*Color.*—Close to 146B to 146C.

Foliage description:

*Arrangement.*—Opposite, simple; generally symmetrical.

*Length, generative plants.*—About 5 cm to 11 cm.

*Width, generative plants.*—About 3.5 cm to 9 cm.

*Shape.*—Ovate.

*Apex.*—Rounded.

*Base.*—Obtuse, rounded.

*Margin.*—Crenate.

*Texture, upper and lower surfaces.*—Glabrous, leathery; succulent.

*Venation pattern.*—Pinnate; reticulate.

*Color.*—Developing leaves, upper surface: Close to 137A. Developing leaves, lower surface: Close to 147B. Fully expanded leaves, upper surface: Close to 147A; venation, close to 137C. Fully expanded leaves, lower surface: Darker than 147B; venation, close to 146A to 146B.

*Petiole.*—Length: About 1 cm to 2 cm. Diameter: About 5 mm. Texture, upper and lower surfaces: Smooth, glabrous. Color, upper surface: Close to 137C. Color, lower surface: Close to 146B.

Flower description:

*Flower arrangement and habit.*—Double flowers arranged singly in compound dichasial cymes that arise from leaf axils. Uniform and freely flowering habit with usually about 12 to 22 flowers developing per inflorescence. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long conditions (at least 14 hours of darkness).

*Time to flower.*—Under short day/long night photoinductive conditions, about 70 days are required. Actual time to flower is primarily dependent upon temperature and light intensity.

*Post-production longevity.*—Excellent post-production longevity; flowers maintain good substance for about six weeks under interior environmental conditions; flowers persistent.

*Inflorescence height.*—About 3.5 cm.

*Inflorescence diameter.*—About 4 cm to 5 cm.

*Flower diameter: About* 1.5 cm.

*Flower length* (*height*).—About 1.1 cm.

*Flower bud.*—Shape: Ovoid. Length: About 8 mm. Diameter: About 3 mm. Color: Close to 18B.

*Petals.*—Arrangement: About 18 fused at the base. Length (largest petals): About 9 mm. Width (largest petals): About 5 mm. Shape: Spatulate. Apex: Apiculate. Margin: Entire. Texture, upper and lower surfaces: Smooth, glabrous; satiny. Color: When opening, upper surface: Initially close to 16C becoming closer to 41C with development. When opening, lower surface: Close to 18B. Fully opened, upper surface: Close to 55B; color becoming closer to 56C to 56D with development. Fully opened, lower surface: Close to 56D.

*Sepals.*—Appearance: Four fused at the base. Length: About 5 mm. Width: About 2 mm. Shape: Lanceolate. Apex: Acute. Margin: Entire. Texture, upper and lower surfaces: Smooth; glabrous. Color, upper and lower surfaces: Close to 144A.

*Peduncles.*—Length: About 3 cm to 6 cm. Diameter: About 2 mm to 4 mm. Aspect: Mostly erect. Strength: Strong. Texture: Smooth, glabrous. Color: Close to 144A.

*Pedicels.*—Length: About 5 mm. Diameter: About 1 mm. Aspect: Erect to about 45° from vertical. Strength: Moderately strong. Texture: Smooth, glabrous. Color: Close to 146B.

*Reproductive organs.*—Androecium: Stamen number: About four per flower. Anther shape: Oval. Anther length: About 1 mm. Anther color: Close to 15B. Amount of pollen: None observed. Gynoecium: Pistil number: About four per flower. Pistil length: About 8 mm. Style length: About 2 mm. Style color: Close to 145A. Stigma shape: Rounded. Stigma color: Close to 151D. Ovary color: Close to 145A.

Seed/fruit.—Seed and fruit development have not been observed.

Temperature tolerance: Plants of the new *Kalanchoe* have been observed to tolerate temperatures from about 5° C. to about 35° C.

Pathogen/pest resistance: Plants of the new *Kalanchoe* have not been observed to be resistant to pests and pathogens common to *Kalanchoes.*

It is claimed:

1. A new and distinct *Kalanchoe* plant named 'Don Darcio' as illustrated and described.

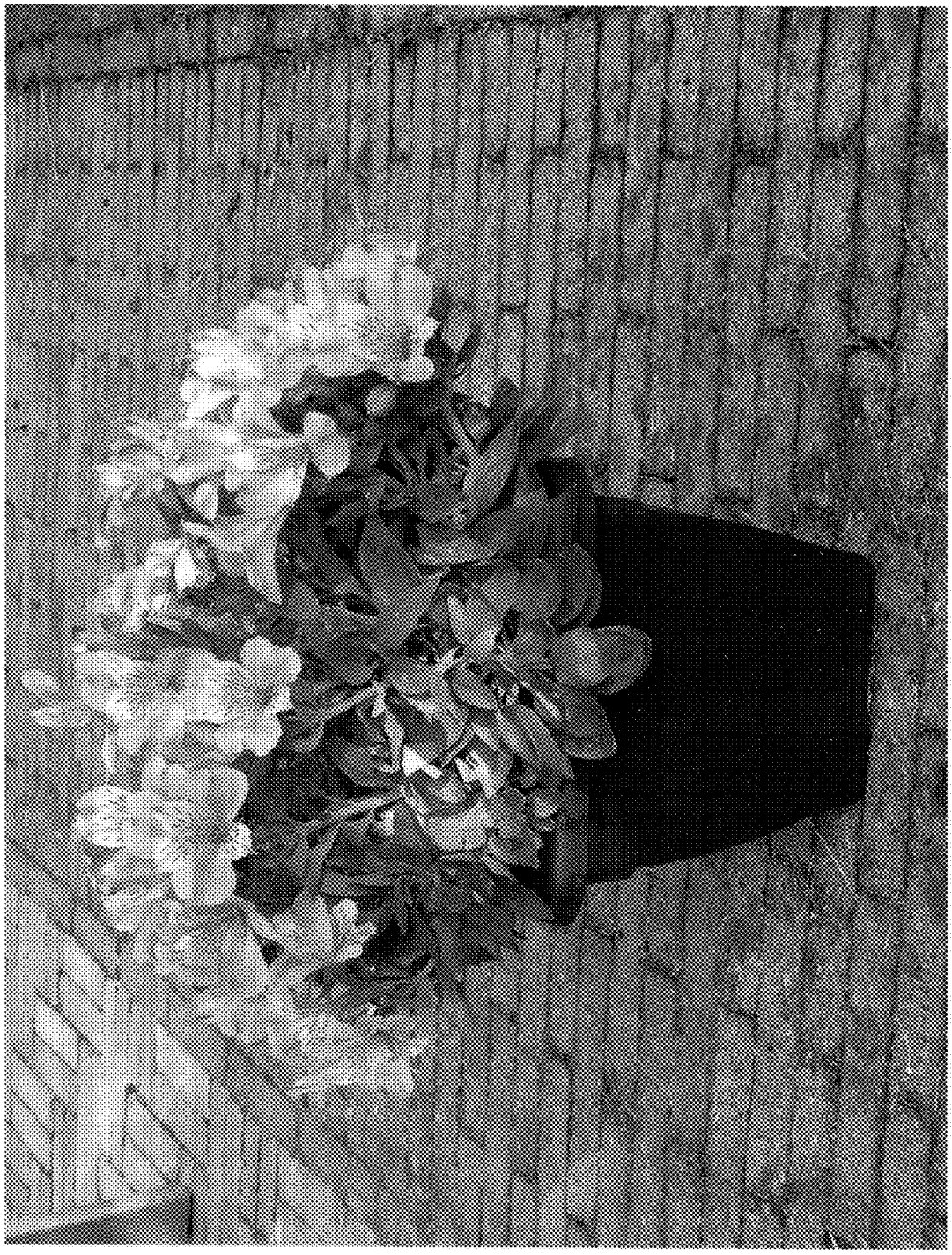

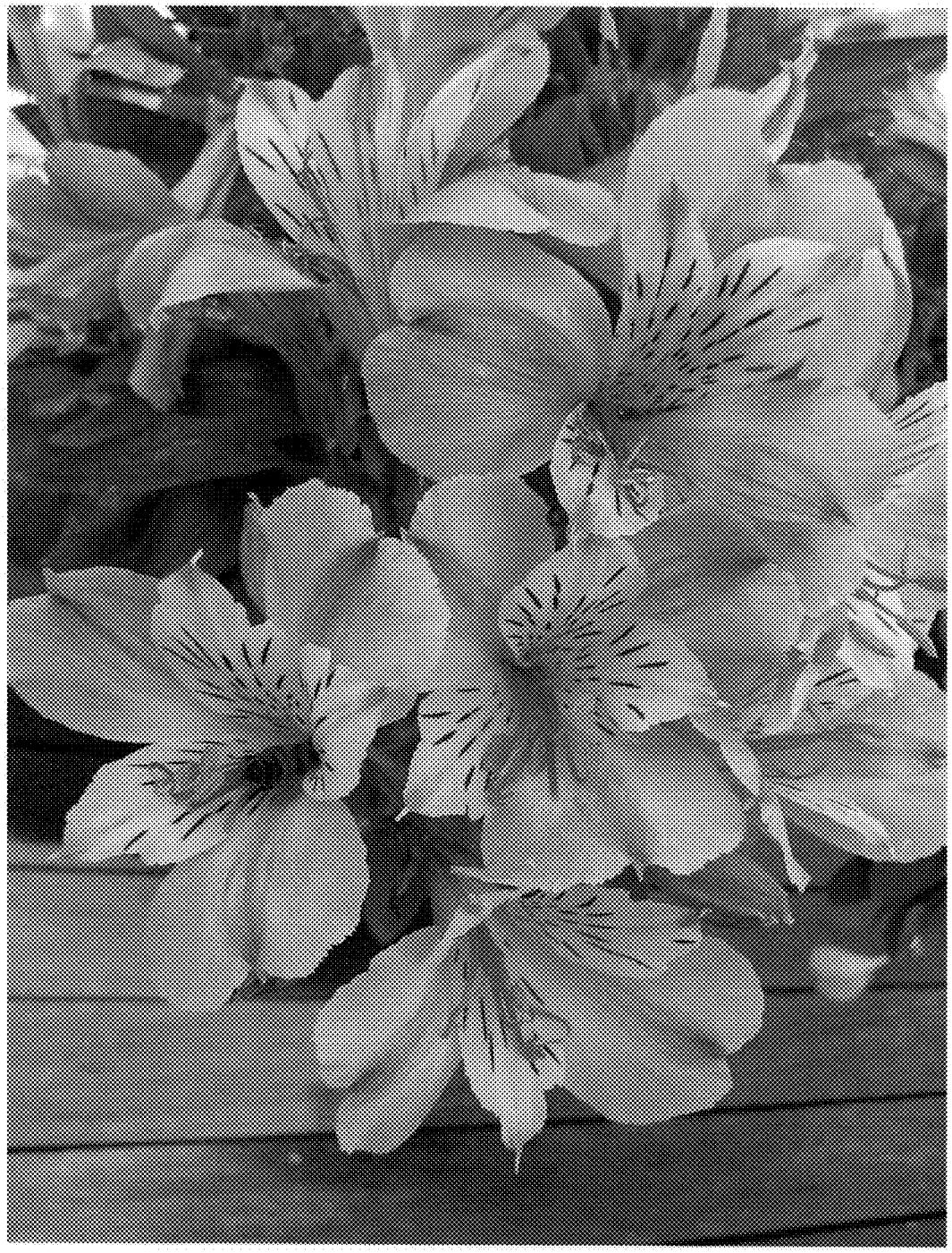

* * * * *